(12) United States Patent
Lorio et al.

(10) Patent No.: US 11,701,242 B2
(45) Date of Patent: Jul. 18, 2023

(54) MINIMALLY INVASIVE INTERVERTEBRAL SYSTEMS AND METHODS

(71) Applicant: EIT Emerging Implant Technologies GmbH, Wurmlingen (DE)

(72) Inventors: Morgan Packard Lorio, Nashville, TN (US); Thomas Purcell, Del Mar, CA (US)

(73) Assignee: EIT Emerging Implant Technologies GmbH, Wurmlingen (DE)

( * ) Notice: Subject to any disclaimer, the term of this patent is extended or adjusted under 35 U.S.C. 154(b) by 568 days.

(21) Appl. No.: 16/841,720

(22) Filed: Apr. 7, 2020

(65) Prior Publication Data

US 2020/0246164 A1 Aug. 6, 2020

Related U.S. Application Data

(60) Continuation of application No. 15/889,100, filed on Feb. 5, 2018, now Pat. No. 10,653,536, which is a
(Continued)

(51) Int. Cl.
*A61B 17/88* (2006.01)
*A61F 2/44* (2006.01)
(Continued)

(52) U.S. Cl.
CPC ............ *A61F 2/4611* (2013.01); *A61F 2/447* (2013.01); *A61F 2/4601* (2013.01);
(Continued)

(58) Field of Classification Search
CPC ...... A61F 2/4611; A61F 2/447; A61F 2/4601; A61F 2310/00023; A61F 2002/2835;
(Continued)

(56) References Cited

U.S. PATENT DOCUMENTS 4,877,020 A 10/1989 Vich
5,171,278 A 12/1992 Pisharodi
(Continued)

FOREIGN PATENT DOCUMENTS

JP 2003-505149 2/2003
JP 2003-526458 9/2003
(Continued)

OTHER PUBLICATIONS

European Extended Search Report and Written Opinion in Application No. 11831342.8, dated Aug. 29, 2014 in 13 pages.
(Continued)

*Primary Examiner* — Eduardo C Robert
*Assistant Examiner* — David C Comstock
(74) *Attorney, Agent, or Firm* — BakerHostetler

(57) ABSTRACT

A minimally invasive intervertebral implant includes a circuitous body defining a luminal axis extending longitudinally therethrough. The circuitous body includes proximal and distal ends oppositely disposed along a lateral axis of the circuitous body. Each of the proximal and distal ends includes an aperture disposed therethrough such that the circuitous body includes a first configuration wherein the proximal and distal ends are at a maximum separation and a second configuration wherein the proximal and distal ends are closer together than in the first configuration.

19 Claims, 9 Drawing Sheets

Related U.S. Application Data continuation of application No. 15/175,032, filed on Jun. 6, 2016, now Pat. No. 9,883,955, which is a division of application No. 13/248,747, filed on Sep. 29, 2011, now Pat. No. 9,358,131.

(60) Provisional application No. 61/389,986, filed on Oct. 5, 2010.

(51) Int. Cl.
   *A61F 2/46* (2006.01)
   *A61F 2/28* (2006.01)
   *A61F 2/30* (2006.01)

(52) U.S. Cl.
   CPC . *A61F 2002/2835* (2013.01); *A61F 2002/305* (2013.01); *A61F 2002/3055* (2013.01); *A61F 2002/30143* (2013.01); *A61F 2002/30331* (2013.01); *A61F 2002/30359* (2013.01); *A61F 2002/30448* (2013.01); *A61F 2002/30462* (2013.01); *A61F 2002/30471* (2013.01); *A61F 2002/30522* (2013.01); *A61F 2002/30545* (2013.01); *A61F 2002/30556* (2013.01); *A61F 2002/30579* (2013.01); *A61F 2002/30593* (2013.01); *A61F 2002/30594* (2013.01); *A61F 2002/30774* (2013.01); *A61F 2002/30828* (2013.01); *A61F 2002/4415* (2013.01); *A61F 2002/4627* (2013.01); *A61F 2310/00023* (2013.01)

(58) Field of Classification Search
   CPC .. A61F 2002/30143; A61F 2002/30359; A61F 2002/30382; A61F 2002/30448; A61F 2002/30462; A61F 2002/30471; A61F 2002/305; A61F 2002/30502; A61F 2002/30504; A61F 2002/30522; A61F 2002/30545; A61F 2002/3055; A61F 2002/30556; A61F 2002/30579; A61F 2002/30598; A61F 2002/30774; A61F 2002/30828; A61F 2002/4415; A61F 2002/4475; A61F 2002/4627
   USPC ............................ 623/17.16; 606/279, 86 A
   See application file for complete search history.

(56) References Cited

U.S. PATENT DOCUMENTS

| | | | |
|---|---|---|---|
| 5,176,587 | A | 1/1993 | Mott |
| 5,549,679 | A | 8/1996 | Kuslich |
| 5,571,189 | A | 11/1996 | Kuslich |
| 5,693,100 | A | 12/1997 | Pisharodi |
| 5,782,832 | A | 7/1998 | Larsen et al. |
| 6,039,761 | A | 3/2000 | Li et al. |
| 6,126,689 | A | 10/2000 | Brett |
| 6,409,766 | B1 | 6/2002 | Brett |
| 6,488,710 | B2 | 12/2002 | Besselink |
| 6,527,804 | B1 | 3/2003 | Gauchet et al. |
| 6,656,178 | B1 | 12/2003 | Veldhuizen et al. |
| 6,893,464 | B2 | 5/2005 | Kiester |
| 7,137,997 | B2 | 11/2006 | Paul |
| 7,445,636 | B2 | 11/2008 | Michelson |
| 7,513,900 | B2 | 4/2009 | Garrison et al. |
| 7,621,950 | B1 | 11/2009 | Globerman et al. |
| 7,621,956 | B2 | 11/2009 | Paul et al. |
| 7,632,278 | B2 | 12/2009 | Jansen et al. |
| 7,641,666 | B2 | 1/2010 | Paul et al. |
| 7,674,296 | B2 | 3/2010 | Rhoda et al. |
| 7,731,751 | B2 | 6/2010 | Butler et al. |
| 7,758,644 | B2 | 7/2010 | Trieu |
| 7,763,028 | B2 | 7/2010 | Lim et al. |
| D623,750 | S | 9/2010 | Duffield et al. |
| 7,846,206 | B2 | 12/2010 | Oglaza et al. |
| 8,021,393 | B2 | 9/2011 | Seifert et al. |
| 8,167,948 | B2 | 5/2012 | Paul et al. |
| D665,081 | S | 8/2012 | Hansell et al. |
| 8,241,358 | B2 | 8/2012 | Butler et al. |
| 8,268,001 | B2 | 9/2012 | Butler et al. |
| 8,394,145 | B2 | 3/2013 | Weiman |
| 8,398,713 | B2 | 3/2013 | Weiman |
| 8,435,298 | B2 | 5/2013 | Weiman |
| 8,454,623 | B2 | 6/2013 | Patel et al. |
| 8,460,386 | B2 | 6/2013 | Ankney et al. |
| 8,496,713 | B2 | 7/2013 | Bennett et al. |
| 8,523,944 | B2 * | 9/2013 | Jimenez ................. F16M 11/38 623/17.15 |
| 8,545,566 | B2 | 10/2013 | Niemiec et al. |
| 8,778,027 | B2 | 7/2014 | Medina |
| 8,808,385 | B1 | 8/2014 | Smith et al. |
| 9,039,768 | B2 | 5/2015 | Voellmicke |
| 9,358,131 | B2 | 6/2016 | Lorio et al. |
| 2001/0012942 | A1 | 8/2001 | Estes et al. |
| 2001/0032020 | A1 | 10/2001 | Besselink |
| 2002/0156481 | A1 | 10/2002 | Boyd et al. |
| 2002/0156529 | A1 | 10/2002 | Li et al. |
| 2003/0236520 | A1 | 12/2003 | Lim et al. |
| 2004/0059421 | A1 | 3/2004 | Glenn et al. |
| 2004/0193158 | A1 | 9/2004 | Lim et al. |
| 2004/0254644 | A1 * | 12/2004 | Taylor .................... A61F 2/4425 623/17.13 |
| 2005/0021041 | A1 | 1/2005 | Michelson |
| 2005/0070911 | A1 | 3/2005 | Carrison et al. |
| 2005/0113920 | A1 | 5/2005 | Foley et al. |
| 2005/0130929 | A1 | 6/2005 | Boyd |
| 2005/0182416 | A1 | 8/2005 | Lim et al. |
| 2006/0004455 | A1 | 1/2006 | Leonard et al. |
| 2006/0030943 | A1 * | 2/2006 | Peterman ................ A61F 2/447 623/17.11 |
| 2006/0036273 | A1 * | 2/2006 | Siegal ................. A61B 17/1757 606/190 |
| 2006/0142858 | A1 | 6/2006 | Colleran et al. |
| 2006/0217806 | A1 * | 9/2006 | Peterman ................ A61F 2/447 606/90 |
| 2007/0233153 | A1 | 10/2007 | Shipp et al. |
| 2007/0282441 | A1 * | 12/2007 | Stream .................... A61B 17/92 623/17.11 |
| 2008/0015701 | A1 | 1/2008 | Garcia et al. |
| 2008/0058933 | A1 * | 3/2008 | Garner .................... A61F 2/447 623/17.11 |
| 2008/0114367 | A1 | 5/2008 | Meyer |
| 2008/0140207 | A1 * | 6/2008 | Olmos .................. A61F 2/4611 623/17.11 |
| 2008/0208255 | A1 * | 8/2008 | Siegal ................. A61B 17/7094 606/279 |
| 2008/0243255 | A1 | 10/2008 | Butler et al. |
| 2008/0312743 | A1 | 12/2008 | Vila et al. |
| 2009/0143859 | A1 | 6/2009 | McClellan et al. |
| 2009/0157187 | A1 | 6/2009 | Richelsoph |
| 2009/0270873 | A1 | 10/2009 | Fabian |
| 2009/0281628 | A1 | 11/2009 | Oglaza et al. |
| 2009/0306672 | A1 | 12/2009 | Reindel et al. |
| 2010/0137987 | A1 | 6/2010 | Diao et al. |
| 2010/0174373 | A1 | 7/2010 | Galley et al. |
| 2010/0209184 | A1 * | 8/2010 | Jimenez .................... E05D 1/02 403/291 |
| 2011/0029085 | A1 * | 2/2011 | Hynes .................... A61F 2/447 623/17.16 |
| 2011/0066192 | A1 * | 3/2011 | Frasier .................. A61F 2/4465 606/86 A |
| 2011/0093072 | A1 * | 4/2011 | Siegal .................... A61B 17/68 623/11.11 |
| 2011/0125270 | A1 | 5/2011 | Paul et al. |
| 2011/0251692 | A1 | 10/2011 | McLaughlin et al. |
| 2011/0276142 | A1 | 11/2011 | Niemiec et al. |
| 2011/0295370 | A1 | 12/2011 | Suh et al. |
| 2012/0016371 | A1 | 1/2012 | O'Halloran et al. |
| 2012/0016481 | A1 | 1/2012 | Zwirkoski |
| 2012/0059470 | A1 | 3/2012 | Weiman |
| 2012/0059475 | A1 | 3/2012 | Weiman |
| 2012/0083887 | A1 | 4/2012 | Purcell et al. |

(56) References Cited

U.S. PATENT DOCUMENTS

| | | |
|---|---|---|
| 2012/0083889 A1 | 4/2012 | Purcell et al. |
| 2012/0123544 A1 | 5/2012 | Suh et al. |
| 2012/0123546 A1 | 5/2012 | Medina |
| 2012/0209386 A1 | 8/2012 | Triplett et al. |
| 2012/0215314 A1 | 8/2012 | Bennett et al. |
| 2013/0018467 A1 | 1/2013 | Suh |
| 2013/0041471 A1 | 2/2013 | Siegal et al. |
| 2013/0144391 A1 | 6/2013 | Siegal et al. |
| 2013/0325128 A1 | 12/2013 | Perloff et al. |
| 2014/0031940 A1 | 1/2014 | Banouskou |

FOREIGN PATENT DOCUMENTS

| | | |
|---|---|---|
| JP | 2008-512218 A | 4/2008 |
| WO | 01/68005 | 9/2001 |
| WO | 2007/076377 A2 | 7/2007 |
| WO | 2008/152501 A2 | 12/2008 |
| WO | 2009/125242 A1 | 10/2009 |
| WO | 2010/103344 A1 | 9/2010 |
| WO | 2012/007918 A2 | 1/2012 |
| WO | 2012/135764 A1 | 10/2012 |
| WO | 2014/035835 A1 | 3/2014 |

OTHER PUBLICATIONS

International Search Report and Written Opinion for PCT/US2011/054001 in 15 pages dated Jan. 17, 2012.
International Search Report and Written Opinion for PCT/US2011/054729 in 13 pages, dated Jan. 31, 2012.
International Search Report and Written Opinion in PCT Application No. PCT/US2013/056500 dated Dec. 6, 2013 in 16 pages.

* cited by examiner

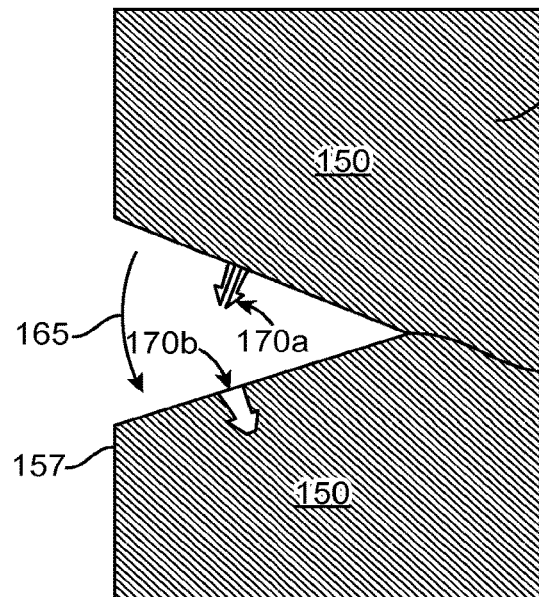 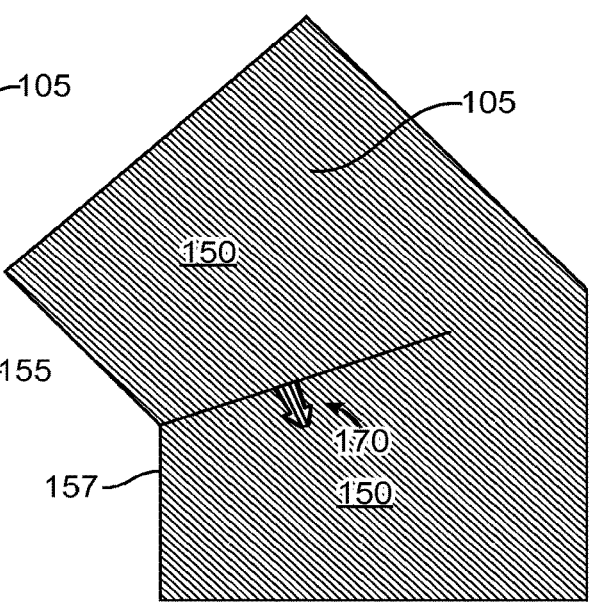
FIG. 5A
FIG. 5B
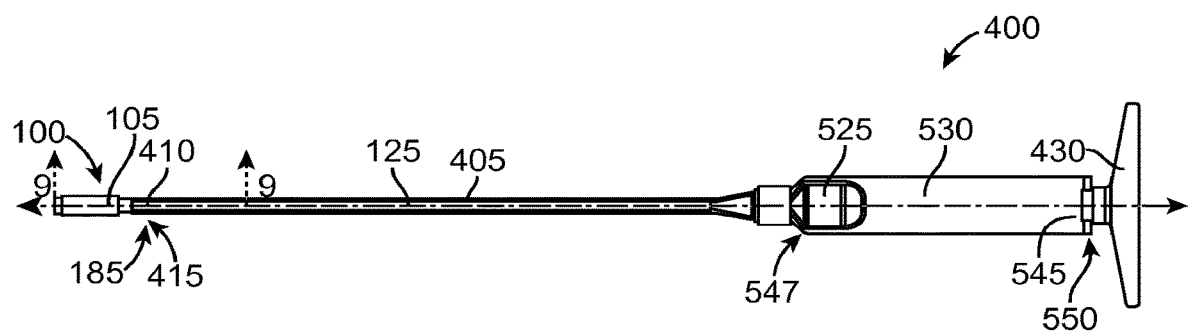
FIG. 6

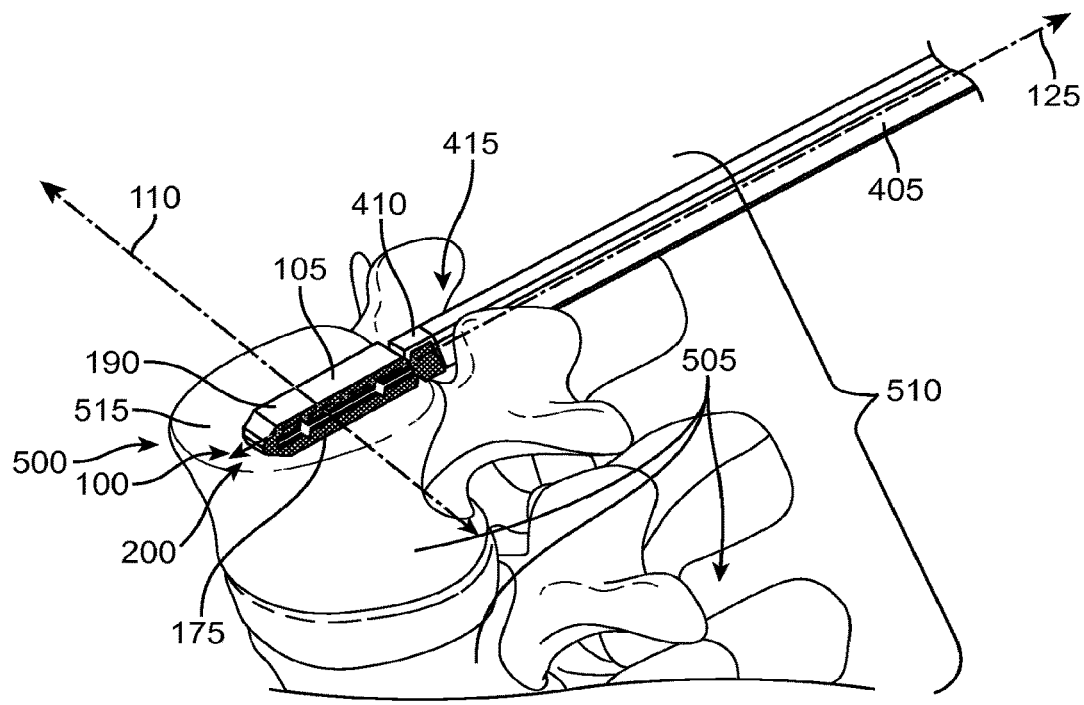
FIG. 11
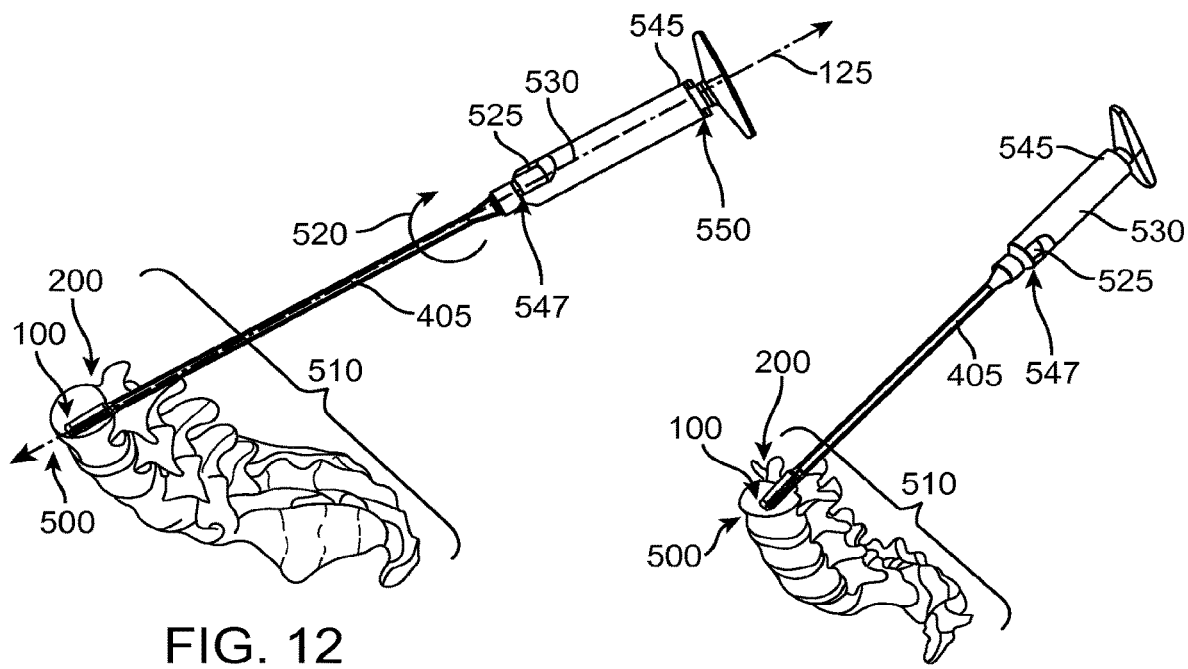
FIG. 12
FIG. 13

MINIMALLY INVASIVE INTERVERTEBRAL SYSTEMS AND METHODS

CROSS-REFERENCE TO RELATED APPLICATIONS

The present application is a continuation of U.S. patent application Ser. No. 15/889,100, filed Feb. 5, 2018, which is a continuation of U.S. patent application Ser. No. 15/175,032, filed Jun. 6, 2016, which is a divisional application of U.S. patent application Ser. No. 13/248,747, filed Sep. 29, 2011, which claims priority to U.S. Provisional Patent Application No. 61/389,986, filed Oct. 5, 2010, the entire contents of each of which are hereby expressly incorporated by reference.

FIELD

The present invention relates generally to a device for treating intervertebral injuries and, more specifically relates to a minimally invasive intervertebral implant that is plastically deformable to enhance bone graft volume and contact with vertebral endplates.

BACKGROUND

Current intervertebral devices are designed using three major principles: the anatomical limitations of the surgical approach, optimization of bone graft volume to promote bony fusion, and optimization of the device contact with vertebral endplates to resist subsidence. Current devices are generally static in that they cannot change shape or volume. Thus, current devices are limited by anatomy and technique and consequently may not provide optimal bone graft volume or surface contact.

A need exists for an intervertebral device or implant that can change shape and/or volume. Such a device benefits from the ability to be advanced to an implantation site in a first configuration having a reduced transverse dimension and subsequently transitioned to a second configuration having a desired transverse dimension at the implantation site. Such a device benefits from a rigid structure that can be held in the second configuration by plastic deformation of the material and/or a mechanism for locking the device in the second configuration. Such a device further benefits from being quickly implantable by a simple tool that places and positions the implant at the implantation site and further delivers bone graft material to fill an interior volume of the implant.

SUMMARY OF THE INVENTION

In one aspect of the present invention, a minimally invasive intervertebral implant includes a circuitous body defining a luminal axis extending longitudinally therethrough, the circuitous body comprising a plurality of segments linked by living hinges configured to deform in transition from an open position to a closed position, at least one of the living hinges includes a locking mechanism on adjacent hinged segments comprising a male fitting configured to engage a female fitting for locking the hinge. Proximal and distal ends oppositely disposed along a lateral axis of the circuitous body includes a first configuration wherein the proximal and distal ends are at a maximum separation and a second configuration wherein the proximal and distal ends are closer together than in the first configuration. Wherein a transition from the first configuration to the second configuration deforms the circuitous body and the engagement of the male and female fittings are configured to maintain the second configuration subsequent to the transition In another aspect of the present invention, a minimally invasive intervertebral implant includes a circuitous body defining a luminal axis extending longitudinally therethrough, the circuitous body comprising a plurality of segments linked by living hinges configured to deform in transition from an open position to a closed position, at least one of the living hinges includes a locking mechanism on adjacent hinged segments comprising living hinges configured to plastically deform for locking in the closed position. Proximal and distal ends oppositely disposed along a lateral axis of the circuitous body includes a first configuration wherein the proximal and distal ends are at a maximum separation and a second configuration wherein the proximal and distal ends are closer together than in the first configuration. Wherein the plastically deformed hinges are configured provide sufficient plastic deformation such that the circuitous body maintains the second configuration subsequent to the transition.

In a further aspect of the present invention, a minimally invasive intervertebral implant includes a circuitous body defining a luminal axis extending longitudinally therethrough, the circuitous body comprising a plurality of segments linked by living hinges configured to deform in transition from an open position to a closed position, at least one of the living hinges includes a locking mechanism on adjacent hinged segments comprising a contact adhesive on the adjacent living hinge for locking in the closed position. Proximal and distal ends oppositely disposed along a lateral axis of the circuitous body includes a first configuration wherein the proximal and distal ends are at a maximum separation and a second configuration wherein the proximal and distal ends are closer together than in the first configuration. Wherein a transition from the first configuration to the second configuration deforms the circuitous body and the living hinge contact adhesive is configured to lock the hinge in the closed position to maintain the second configuration subsequent to the transition.

BRIEF DESCRIPTION OF THE FIGURES

FIG. 5A illustrates a living hinge having a locking mechanism in an open position.

FIG. 5B illustrates the living hinge of FIG. 5A in a locked position.

FIG. 6 illustrates a minimally invasive intervertebral implant attached to an embodiment of an implantation tool.

FIG. 11 illustrates an embodiment of a minimally invasive intervertebral implant positioned at an implantation site such that a luminal axis of the implant is generally parallel with a bone surface at the implantation site.

FIG. 12 illustrates the minimally invasive intervertebral implant at the implantation site of FIG. 11 before rotation.

FIG. 13 illustrates the minimally invasive intervertebral implant at the implantation site of FIG. 11 after rotation such that the luminal axis of the implant is generally perpendicular to the bone surface.

The foregoing and other features and advantages of the invention are apparent from the following detailed description of exemplary embodiments, read in conjunction with the accompanying drawings; wherein like structural or functional elements may be designated by like reference numerals.

DETAILED DESCRIPTION

The words proximal and distal are applied to denote specific ends of components of the current invention described herein. A proximal end refers to the end of a component nearer to a medical professional when the component is implanted. A distal end refers to the end of a component further from the medical professional when the component is implanted.

Figure 1:
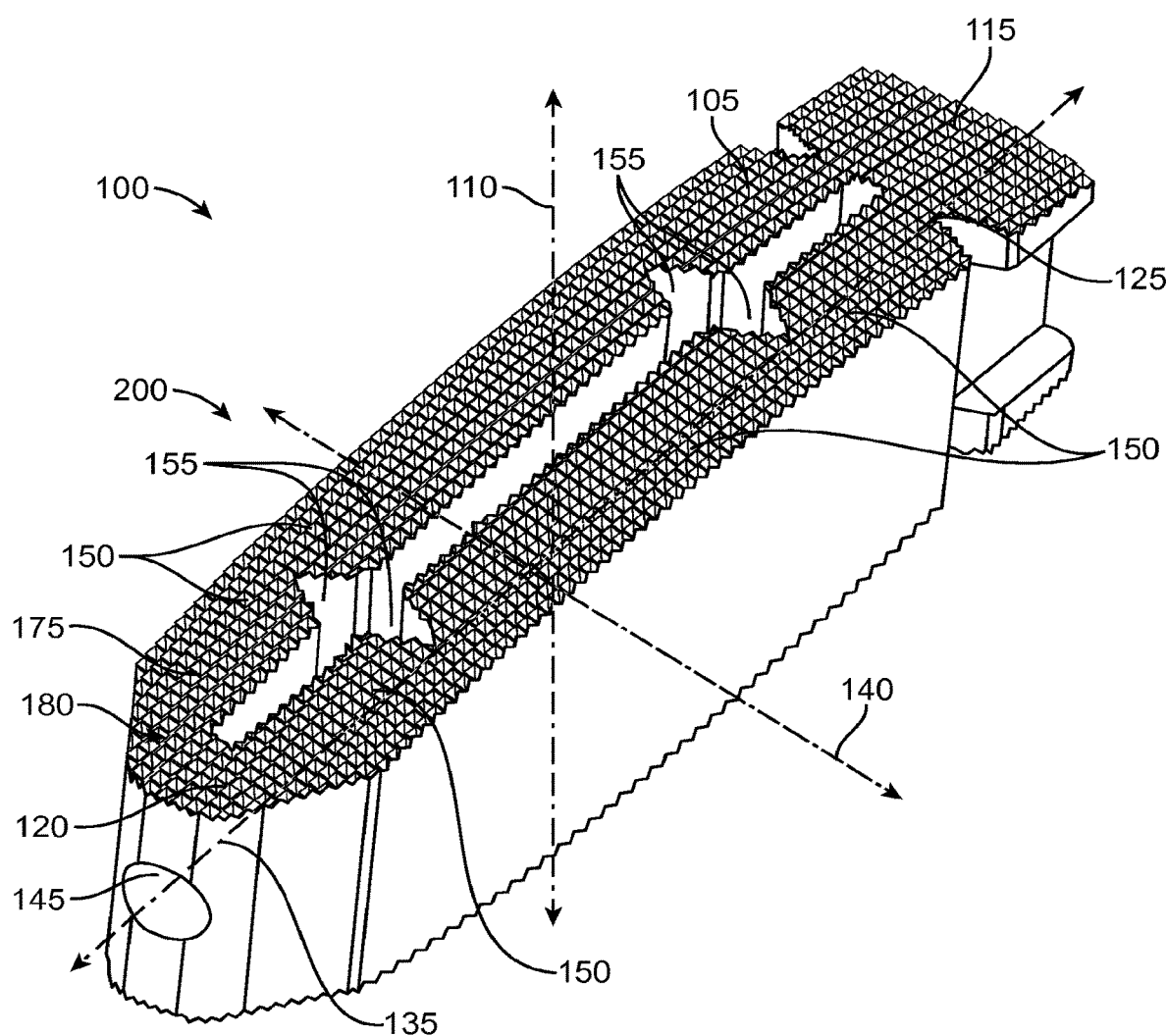
FIG. 1 is an isometric view of an embodiment of a minimally invasive intervertebral implant in a first configuration.

Referring to FIGS. 1-4, an embodiment of a minimally invasive intervertebral implant 100 includes a circuitous body 105 defining a luminal axis 110 extending longitudinally therethrough, as illustrated in FIG. 1. The circuitous body 105 includes a proximal end 115 and a distal end 120 that are oppositely disposed along a lateral axis 125 of the circuitous body 105. As best visible in FIG. 2C, a proximal aperture 130 is disposed through the proximal end 115 of the circuitous body 105 and a distal aperture 135 is disposed through the distal end 120 of the circuitous body 105. A transverse axis 140 that is orthogonal to the luminal axis 110 and the lateral axis 125, as illustrated in FIG. 1, is defined for convenience of description herein. In one embodiment, threads (not shown) are disposed on a luminal surface 145 of the distal aperture 135.

Figure 2A:
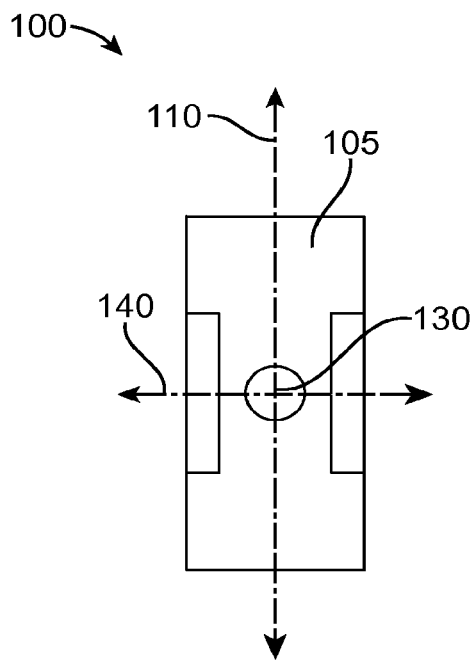
FIG. 2A is a lateral elevation of the minimally invasive intervertebral implant of FIG. 1 in the first configuration.
Figure 2B:
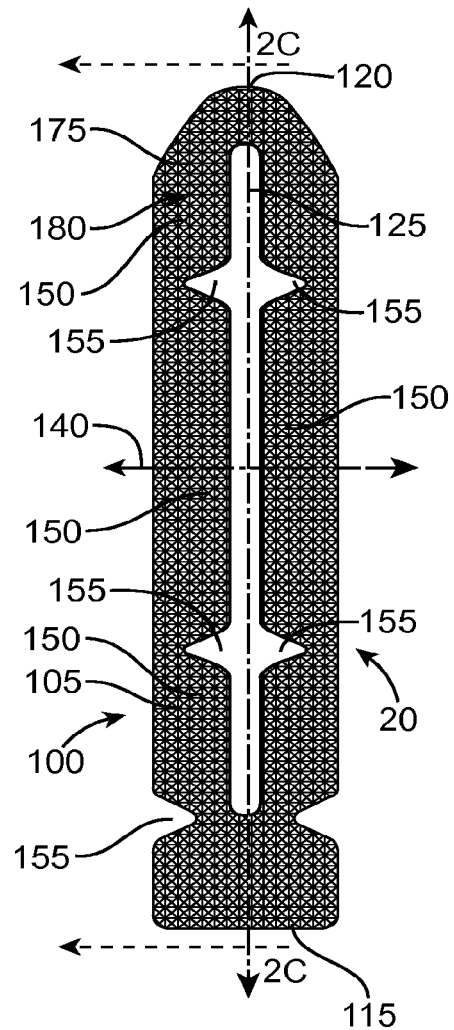
FIG. 2B is a luminal elevation of the minimally invasive intervertebral implant of FIG. 1 in the first configuration.
Figure 2C:
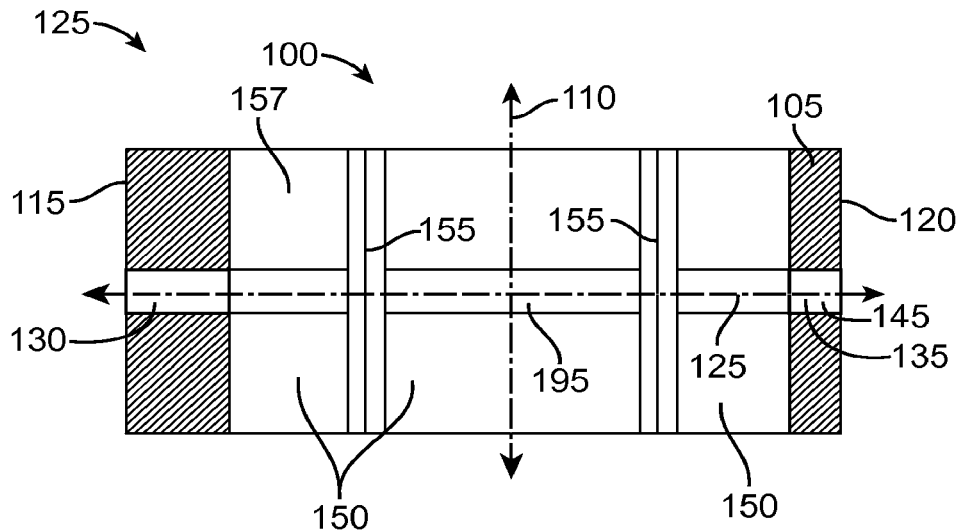
FIG. 2C is a cross-sectional view of the minimally invasive intervertebral implant, taken generally along the line 2C-2C of FIG. 2B.
Figure 3:
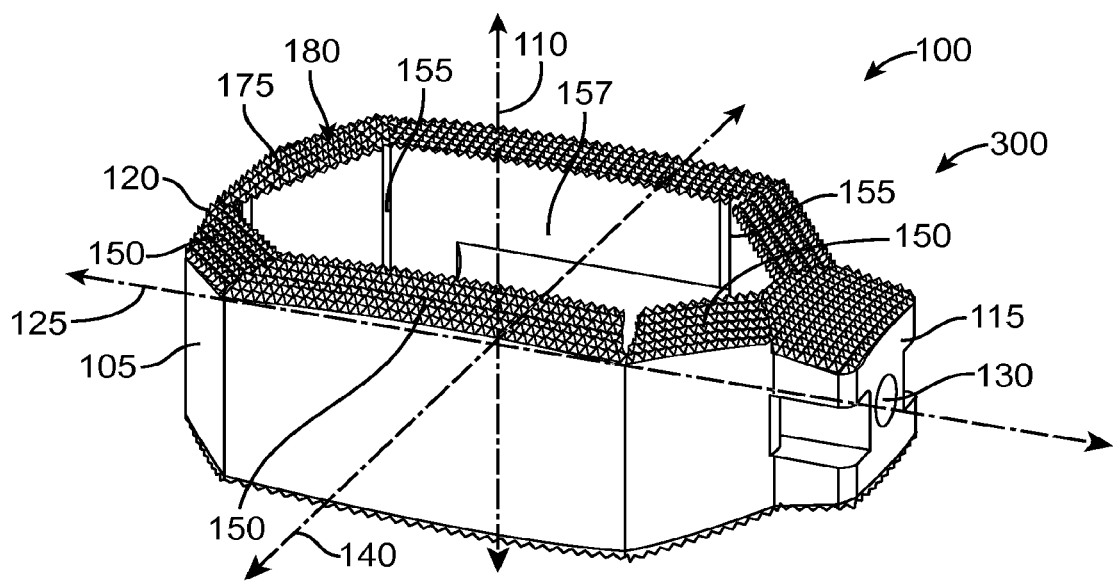
FIG. 3 is an isometric view of the minimally invasive intervertebral implant of FIG. 1 in a second configuration.
Figure 4:
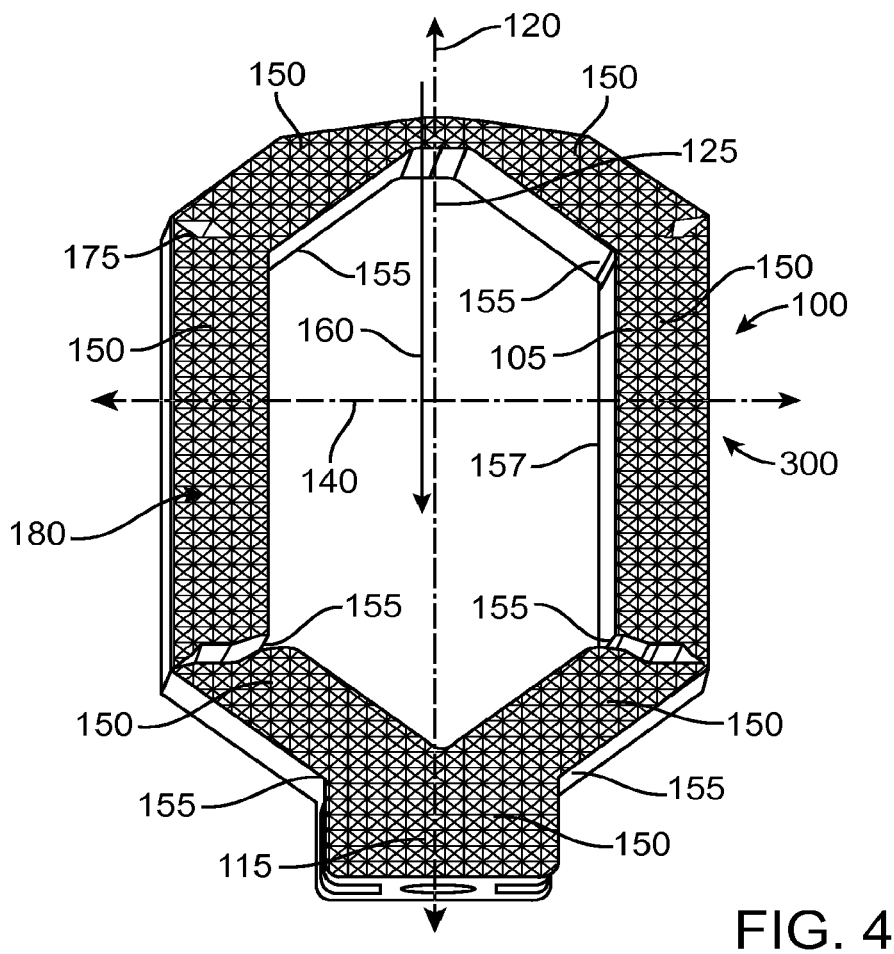
FIG. 4 is a luminal elevation of the minimally invasive intervertebral implant of FIG. 1 in the second configuration.
Figure 7:
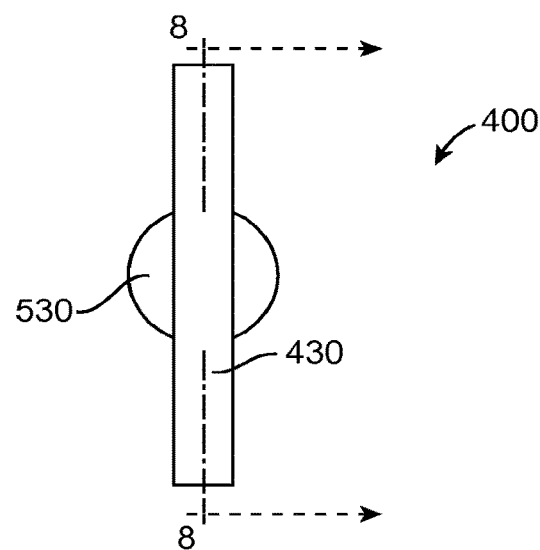
FIG. 7 is a proximal elevation of the implantation tool of FIG. 6.
Figure 8:
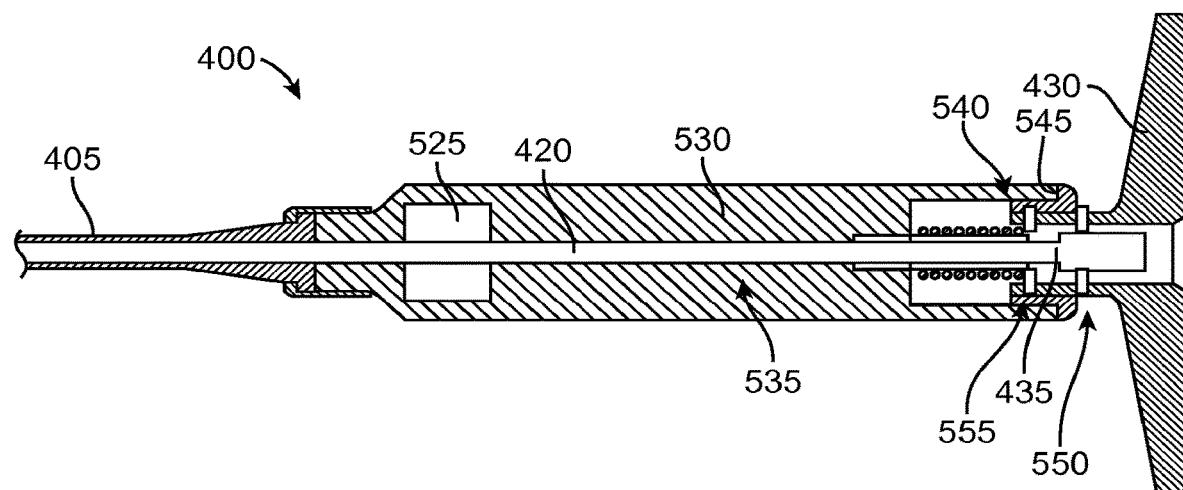
FIG. 8 is a cross-sectional view of the implantation tool, taken generally along the line 8-8 of FIG. 7.
Figure 9:
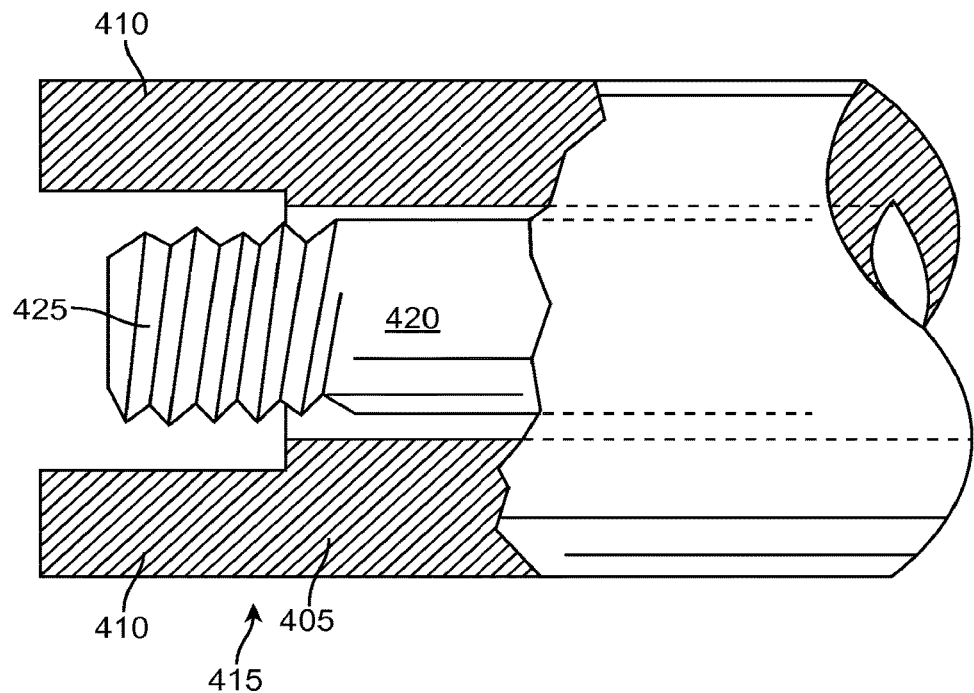
FIG. 9 is an enlarged cross-sectional view of a distal end of the implantation tool, taken generally along the line 9-9 of FIG. 6.

The circuitous body 105 includes a first configuration 200 wherein the proximal and distal ends 115, 120 are at a maximum separation, as best illustrated by FIGS. 1 and 2B. Referring to FIGS. 3 and 4, the circuitous body 105 includes a second configuration 300 wherein the proximal and distal ends 115, 120 are separated by less than a maximum separation and are therefore closer together than in the first configuration. The circuitous body 105 may be held in the second configuration by plastic deformation of the material.

In one embodiment, the circuitous body 105 comprises a rigid biologically inert material, including by way of example and not limitation, titanium, titanium alloy, and polyetherketoneketone (PEEK). The circuitous body 105 may transition from the first configuration 200 to the second configuration 300 via elastic or plastic deformation. It is preferable that the circuitous body 105 maintains the second configuration 300 subsequent to a transition thereto as would be the case if the transition from the first configuration 200 to the second configuration 300 plastically deforms the circuitous body 105. Applying sufficient force on the distal end 120 toward the proximal end 115, as depicted by arrow 160 in FIG. 4, causes the circuitous body 105 to transition from the first configuration 200 to the second configuration 300.

Referring to FIGS. 1, 2B, 3, and 4, in one embodiment, the circuitous body 105 comprises a single piece unit having segments 150 that are linked by living hinges 155 that are disposed in an interior surface 157 of the circuitous body 105 and that may plastically deform in the transition from the first configuration 200 to the second configuration 300. As illustrated in FIGS. 1, 2B, and 5A, when the circuitous body 105 is in the first configuration 200, the living hinges 155 are in an open position. As illustrated in FIGS. 3, 4, and 5B, upon transition to the second configuration 300, the segments 150 rotate relative to one another, as depicted by the arrow 165 in FIG. 5A, such that the living hinges 155 are in a closed position.

In some embodiments, plastic deformation of the living hinges 155 from the open position as illustrated in FIGS. 1, 2B, and 5A to the closed position as illustrated in FIGS. 3, 4, and 5B may provide sufficient plastic deformation such that the circuitous body 105 maintains the second configuration 300 subsequent to a transition thereto. In other embodiments, a locking mechanism 170, for example, male and female compressive snap fittings 170a, 170b, may be provided, as illustrated in FIGS. 5A and 5B. In this embodiment, barbed ends of the male compressive snap fitting 170a are compressed toward one another upon entry into the female compressive snap fitting 170b. Ultimately, as the segments 150 rotate such that the living hinge 155 reaches the closed position as illustrated in FIGS. 3, 4, and 5B, the barbed ends of the male compressive snap fitting reach a depth beyond a set of internal shoulders within the female compressive snap fitting at which point the barbed ends spring apart and are permanently captured by the internal shoulders.

Other locking mechanisms 170 may be utilized to maintain the circuitous body 105 in the second configuration 300 subsequent to a transition thereto, including by way of example and not limitation, contact adhesive, a single barbed male fitting engaging a female fitting, etc. It is contemplated that the locking mechanism 170 may also comprise a ratchet mechanism (not shown), whereby the female compressive snap fitting 170b includes multiple sets of internal shoulders at increasing depths such that the living hinge 155 can be locked in any of several positions between a fully open position as illustrated in FIGS. 1, 2B, and 5A and a fully closed position as illustrated in FIGS. 3, 4, and 5B.

Referring to FIGS. 1, 2B, 3, and 4, in some embodiments, at least one longitudinally facing surface 175 of the circuitous body 105 includes a texture 180 adapted to enhance fixed contact with a bone surface. Further, referring to FIGS. 1, 2A and 3, the proximal end 115 of the circuitous body 105 includes a pair of proximally extending slots 185 oppositely disposed in exterior surfaces 190 of the proximal end 115. As will be fully described hereinbelow, the slots 185 are adapted to accommodate prongs (See FIGS. 6 and 9-11) of an implantation tool (See FIGS. 6-9, 12, 13, and 16).

Figure 16:
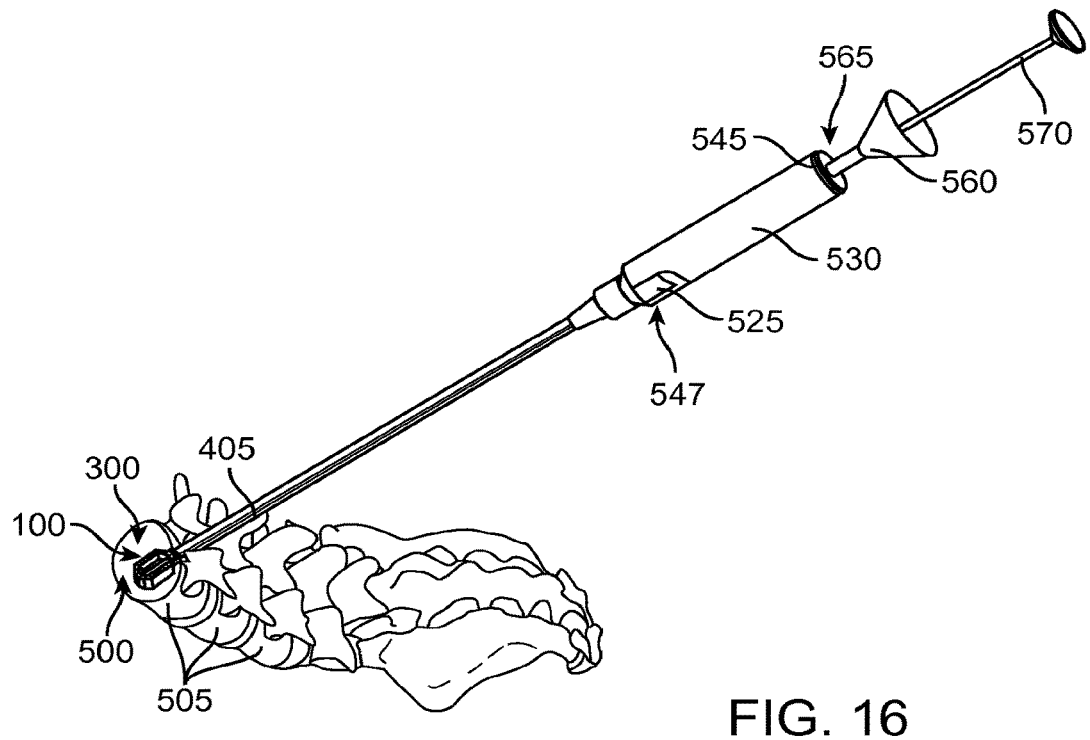
FIG. 16 illustrates the minimally invasive intervertebral implant at the implantation site of FIG. 11 in the second configuration being filled with bone graft material by the implantation tool with the shaft and handle replaced by a funnel and plunger.

Referring to FIGS. 6-9, an embodiment of an implantation tool 400 for the minimally invasive intervertebral implant 100 includes a cannula 405 having a pair of prongs 410 extending distally from a distal end 415 of the cannula 405 to engage the slots 185 in the circuitous body 105. Referring to FIGS. 8-10D, the implantation tool 400 includes a shaft 420 adapted to be slidably disposed longitudinally through the cannula 405. In one embodiment, the shaft 420 includes a threaded distal end 425 adapted to engage threads (not shown) disposed on the luminal surface 145 of the distal aperture 135 of the circuitous body 105. In other embodiments, the distal end 425 includes other removable fastening mechanisms for attachment to the luminal surface 145 of the distal aperture 135, including by way of example and not limitation, a keyed aperture, a bayonet slot, and the like. A handle 430 is attached to a proximal end 435 of the shaft 420. Referring to FIG. 16, the implantation tool 400 further includes a plunger and a funnel, which will be fully described hereinbelow with regard to a method for implantation of the minimally invasive intervertebral implant 100.

Figure 10A:
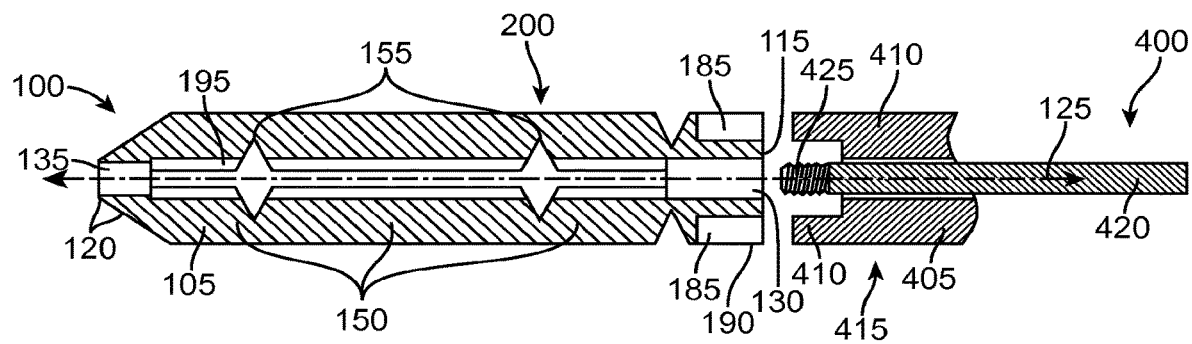
FIG. 10A is a cross-sectional view of the minimally invasive intervertebral implant in the first configuration and the distal end of the implantation tool prior to attachment, taken generally along the line 9-9 of FIG. 6.

As illustrated in FIGS. 10A-10D, the implantation tool 400 functions to transition the circuitous body 105 from the first configuration 200 to the second configuration 300. Further, as illustrated in FIGS. 11-16, the implantation tool 400 functions to facilitate placement, orientation, and filling of the minimally invasive intervertebral implant 100 at an implantation site. Referring to FIG. 10A, in a first step, the minimally invasive vertebral implant 100 is in the first configuration 200. The distal end 415 of the cannula 400 is brought near the proximal end 115 of the circuitous body 105 such that the pair of prongs 410 is aligned with the pair of slots 185. Next, the cannula 405 is advanced distally relative to the minimally invasive intervertebral implant 110, as illustrated by arrow 440 in FIG. 10B, such that the pair of prongs 410 engages the pair of proximally extending slots 185.

Figure 10B:
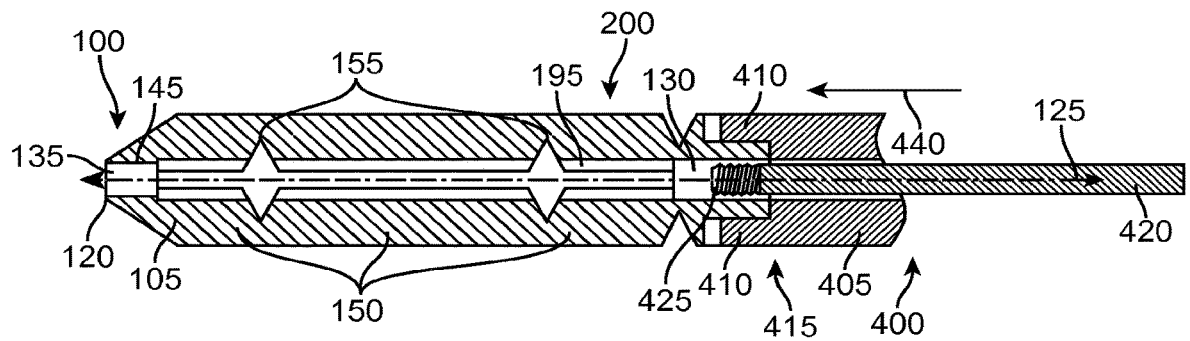
FIG. 10B is the view of FIG. 10A illustrating the prongs of the implantation tool engaging the slots of the minimally invasive intervertebral implant.

At the point in the method illustrated in FIG. 10B, the cannula 405 is connected to the proximal end 115 of the circuitous body 105 such that rotation of the cannula 405 results in rotation of the circuitous body 105. Such rotation is independent of the shaft 420 that is free to rotate and translate along the lateral axis 135 within the cannula 405.

Figure 10C:
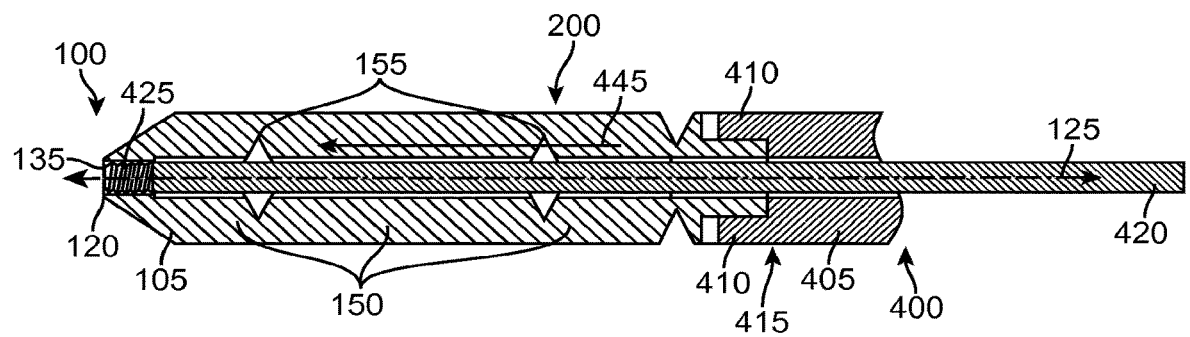
FIG. 10C is the view of FIG. 10B illustrating the threaded tip of the shaft of the implantation tool engaging the distal aperture of the minimally invasive intervertebral implant.

Referring to FIG. 10C, the shaft 420 is advanced distally relative to the cannula 405 such that the distal end 425 of the shaft 420 passes through the proximal aperture 130. Referring to FIGS. 2C, 10A, 10B, and 10D, in one embodiment, an internal groove 195 is disposed extending laterally along the lateral axis 125 in the interior surface 157 of the circuitous body 105. The internal groove 195 provides clearance for the shaft 420 passing across the circuitous body from the proximal aperture 130 to the distal aperture 135. Such clearance allows the circuitous body 105 to be transversely compressed in the first configuration 200. Such transverse compression may allow the circuitous body 105 to fit into a smaller space, for example, an intervertebral space, than might be possible if the internal groove 195 were not present.

Figure 10D:
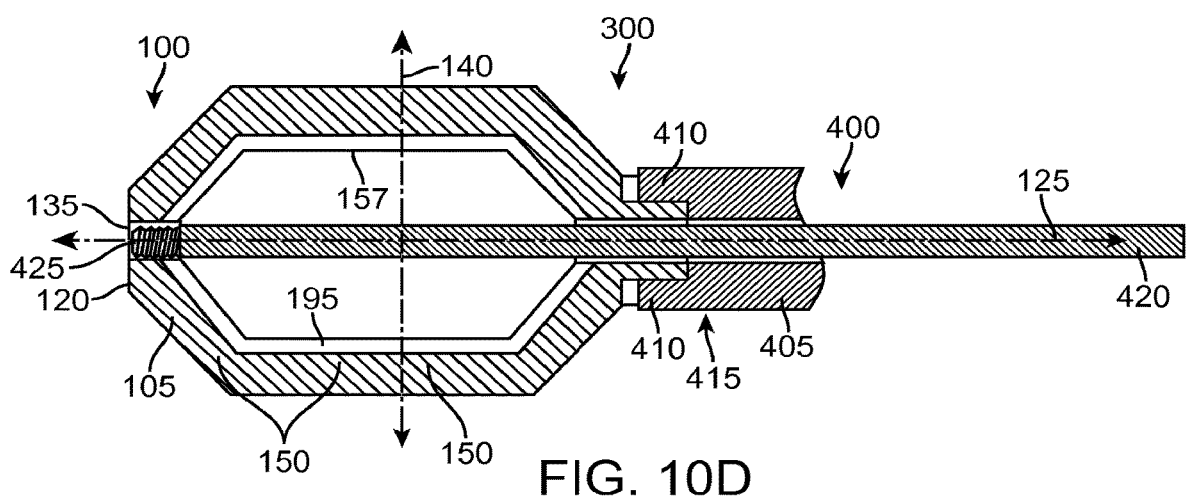
FIG. 10D is the view of FIG. 10C illustrating the minimally invasive intervertebral implant transitioned to the second configuration.

The shaft 420 is further advanced distally relative to the cannula 405, as illustrated by arrow 445 in FIG. 10C, until the distal end 425 passes into the distal aperture 135. In this embodiment, the distal end 425 and the luminal surface 145 of the distal aperture 135 may threadably engage via rotation of the shaft 420 relative to the cannula 405 using the handle 430 that is attached to the proximal end 435 of the shaft 420. Referring to FIG. 10D, following connection of the distal end 425 of the shaft 420 to the distal aperture 135, a force is applied to the shaft 420 in a proximal direction relative to the cannula 405. In this embodiment, the force is transmitted as a tension force within the shaft 420 effectively applying a laterally compressive force to the circuitous body 105 between the distal aperture 135 and the proximal end 115. Subsequent to transitioning the circuitous body 105 from the first configuration 200 to the second configuration 300, the distal end 425 of the shaft 420 is disconnected from the distal aperture 135 and removed from the cannula 405.

Having described how the implantation tool 400 functions to transition the circuitous body 105 from the first configuration 200 to the second configuration 300 hereinabove with regard to FIGS. 10A-10D, the function of the implantation tool 400 for placement, orientation, and filling of the minimally invasive intervertebral implant 100 at an implantation site will now be described. Referring to FIG. 11, in a first step, the distal end 415 of the implantation tool 400, including the minimally invasive intervertebral implant 100 attached thereto in the first configuration 200 with the distal end 425 of the shaft 420 engaging the distal aperture 135, is advanced to an implantation site 500, for example, at a space between vertebrae 505 of a spine 510. The minimally invasive intervertebral implant 100 is oriented at the implantation site 500 such that the luminal axis 110 of the circuitous body 105 is generally parallel with a bone surface 515 at the implantation site 500.

One reason why the circuitous body 105 is initially oriented as illustrated in FIG. 11 is the relative ease of introduction into an intervertebral space facilitated by such orientation. As known in the art, prior to placement of the minimally invasive intervertebral implant 100 in the intervertebral space, vertebrae on either side of the intervertebral space are distracted. In some methodologies, distraction is accomplished via a tool having paddles that can get in between the vertebrae and can subsequently be spread apart to distract the vertebrae. A tool that may be useful in distracting the vertebrae may, for example, be found in Reindel et al. U.S. Patent Application Publication No. 2009/0306672, which is incorporated by reference herein in its entirety.

Following distraction of the vertebrae, a common procedure includes preparing the intervertebral disc space for introduction of an implant. Preparation may include removal of a portion of a disc annulus or evacuation of a disc nucleus, as known in the art. Further steps may include the removal of cartilaginous endplates on the vertebrae. A tool that may be useful in preparation of an intervertebral disc space for introduction of an implant may be found, for example, in Jansen et al. U.S. Pat. No. 7,632,278, which is incorporated by reference herein in its entirety.

As noted hereinabove, with regard to FIGS. 2C, 10A, 10B, and 10D and the internal groove 195, transverse compression of the circuitous body 105 may allow the circuitous body 105 to fit into a smaller intervertebral space than might be possible if the internal groove 195 were not present. The ability to fit the circuitous body in a smaller space facilitates less distraction of the surrounding vertebrae. Thus, the circuitous body 105 is introduced into the intervertebral disc space such that the exterior surfaces 190 initially face the bone surface 515 and the longitudinally facing surfaces 175 do not face the bone surface 515.

Figure 14:
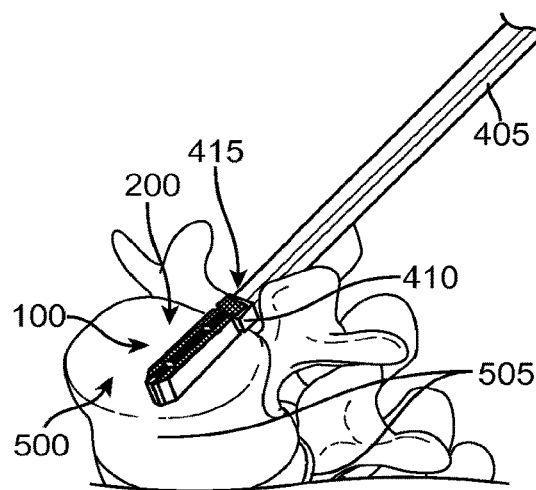
FIG. 14 illustrates the minimally invasive intervertebral implant at the implantation site of FIG. 11 after rotation and prior to being transitioned from the first configuration to the second configuration.

Referring to FIGS. 12 and 13, subsequent to initial placement of the minimally invasive intervertebral implant 100, the circuitous body 105 is rotated by about 90 degrees, as illustrated by arrow 520 in FIG. 12. FIGS. 13 and 14 illustrate the circuitous body 105 subsequent to rotation and in an orientation such that that the longitudinally facing surfaces 175 face the bone surface 515 and the exterior surfaces 190 do not face the bone surface 515.

Referring to FIGS. 6, 8, 12, 13, and 16, in some embodiments, the implantation tool may include a rotational position indicator 525 that is fixedly attached to the cannula 405. Because the cannula is rotationally fixed to the circuitous body 105 via the prongs 410 engaged in the slots 185, the relative rotational position of the circuitous body 105 is reflected by the relative rotational position of the rotational position indicator 525.

Still referring to FIGS. 6, 8, 12, 13, and 16, in another embodiment, the implantation tool 400 may further include a cover member 530 that attaches over a proximal end 535 of the cannula 405 such that a distal end 540 of the handle 430 is accommodated by a proximal end 545 of the cover member 530. The cover member 530 provides a larger surface that may be easier to grab and manipulate by a medical professional. In addition, the cover member is rotationally fixed to the cannula 405 and may include an aperture 547 through which the rotational position indicator is visible.

First and second positional markings 550, 555 are disposed proximate the distal end 540 of the handle 430. When the first marking 550 is visible and the second marking 555 is visibly obstructed by the cover member 530, the distal end 425 of the shaft 420 extends from the distal end 415 of the cannula 405 a first distance that may, for example, correspond to the shaft 420 being operationally attached in the distal aperture 135 of the circuitous body 105 in the first configuration 200. When the first and second markings 550, 555 are both visible, the distal end 425 of the shaft 420 extends from the distal end 415 of the cannula 405 a second distance that may, for example, correspond to the shaft 420 being operationally attached to the distal aperture 135 of the circuitous body 105 in the second configuration 300. Thus, the first and second markings 550, 555 may provide a medical practitioner a visual aide in addition to visualization of the implantation site 500 via other methods known in the art to determine the status of the circuitous body 105.

Figure 15:
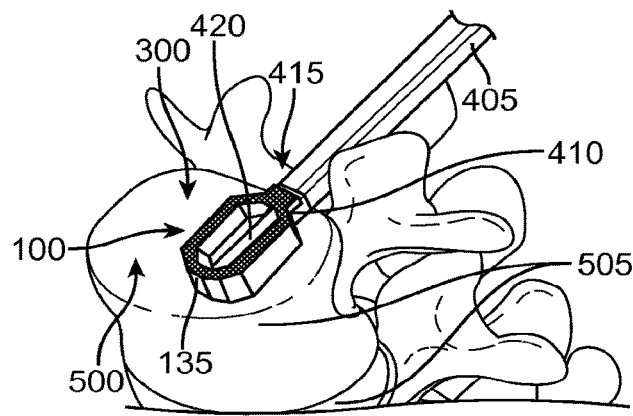
FIG. 15 illustrates the minimally invasive intervertebral implant at the implantation site of FIG. 11 in the second configuration prior to being filled with bone graft material.

Referring again to FIG. 14, the circuitous body 105 is oriented appropriately to undergo transition from the first configuration 200 to the second configuration 300. As illustrated in FIG. 15 and described in detail hereinabove with regard to FIGS. 10A-10D, the circuitous body 105 is transitioned from the first configuration 200 to the second configuration 300 by applying a lateral compression force between the proximal and distal ends thereof.

Referring to FIG. 16, following delivery and orientation of the circuitous body 105 and transition to the second configuration 300, the shaft 420 and handle 430 are removed from the cannula 405, as described in detail hereinabove in regard to FIGS. 10A-10D. In one embodiment, the implantation tool 400 includes a funnel 560 having a distal end 565 adapted to removably attach to the proximal end 535 of the cannula 405. The funnel 560 may attach to the cannula 405 by any method of attachment as known in the art, including by way of example and not limitation, a press fit, a snap fit, a bayonet socket, threads, and the like.

A plunger 570 is adapted to form a sliding seal with a lumen of the funnel 560 for the purpose of forcing bone graft material through the cannula 405 to the implantation site 500 within the circuitous body 105. Thus, in a final step in the method for implantation of a minimally invasive intervertebral implant, bone graft material is forced through the funnel 560 and cannula 405 with the plunger 570 until an interior volume of the minimally invasive vertebral implant 100 is filled.

A minimally invasive intervertebral implant, an implantation tool therefore, and a method for implantation thereof are presented. The implant benefits from the having an expandable geometry, which allows the implant to be placed into intervertebral spaces smaller than typical fixed geometry implants.

It will be appreciated by those skilled in the art that changes could be made to the embodiments described hereinabove without departing from the broad concepts disclosed therein. It is understood, therefore, that this disclosure is not limited to the particular embodiments disclosed, but it is intended to cover modifications that may include a combination of features illustrated in one or more embodiments with features illustrated in any other embodiments. Various modifications, equivalent processes, as well as numerous structures to which the present disclosure may be applicable will be readily apparent to those of skill in the art to which the present disclosure is directed upon review of the present specification. Accordingly, this description is to be construed as illustrative only and is presented for the purpose of enabling those skilled in the art to make and use the minimally invasive intervertebral implant, implantation tool therefor, and method for implantation thereof described herein and to teach the best mode of carrying out the same.

The invention claimed is:

1. A method of implanting an expandable intervertebral implant, the method comprising the steps of:
    inserting the intervertebral implant between adjacent vertebrae in a first configuration, wherein the intervertebral implant includes a plurality of segments linked by living hinges that cooperate to define a circuitous body having a lumen extending therethrough;
    deforming the circuitous body of the intervertebral implant about the living hinges from a first configuration whereby proximal and distal ends of the circuitous body are at a maximum separation along a lateral axis of the circuitous body, to a second configuration whereby the proximal and distal ends are closer together along the lateral axis than in the first configuration;
    wherein the deforming step causes male and female fittings of a locking mechanism of the body to engage to thereby maintain the second configuration after the deforming step.

2. The method of claim 1, wherein at least one of the living hinges includes the locking mechanism.

3. The method of claim 1, wherein the deforming step causes a barbed end of the male fitting to reach a depth beyond internal shoulders of the female fitting so as to lock the body in the second configuration, thereby engaging the male and female fittings.

4. The method of claim 1, wherein the male fitting includes a barbed end and the female fitting includes multiple sets of internal shoulders at increasing depths, wherein the deforming step causes the barbed end of the male fitting to reach a depth beyond the internal shoulders in any of several positions between a fully open position of the living hinge and a fully closed position of the living hinge.

5. The method of claim 1, further comprising the step of coupling an implantation tool to an aperture at the proximal end of the body.

6. The method of claim 5, wherein the coupling step comprises inserting prongs of the implantation tool into a pair of proximally extending slots at the proximal end.

7. The method of claim 1, further comprising the step of causing texture of at least one exterior surface of the body to enhance fixed contact with a respective at least one of the adjacent vertebrae.

8. The method of claim 1, wherein the distal end of the body is tapered.

9. The method of claim 1, wherein the deforming step moves first and second sides of adjacent first and second ones of the segments, respectively, toward each other, and the male and female fittings are defined by respective ones of the first and second sides.

10. A method of implanting an expandable intervertebral implant, the method comprising the steps of:
inserting the intervertebral implant between adjacent vertebrae in a first configuration, whereby the intervertebral implant defines a circuitous body having a plurality of segments linked by living hinges and defining a luminal axis extending longitudinally therethrough, the circuitous body defining a proximal end and a distal end opposite the proximal end along a lateral axis of the circuitous body;
decreasing a distance from the proximal end to the distal end along the lateral axis, thereby deforming the body of the intervertebral implant about the living hinges from the first configuration whereby the proximal and distal ends of the body are at a first separation, to a second configuration whereby the proximal and distal ends are closer together than in the first configuration;
wherein the decreasing step causes the living hinges to deform plastically, such that the living hinges maintain the body in the second configuration after the decreasing step.

11. The method of claim 10, further comprising the step of coupling an implantation tool to an aperture at the proximal end of the body.

12. The method of claim 11, wherein the coupling step comprises inserting prongs of the implantation tool into a pair of proximally extending slots at the proximal end.

13. The method of claim 10, further comprising the step of causing texture of at least one exterior surface of the body to enhance fixed contact with a respective at least one of the adjacent vertebrae.

14. A method of implanting an expandable intervertebral implant, the method comprising the steps of:
inserting the intervertebral implant between adjacent vertebrae, wherein the intervertebral implant includes a body having a plurality of segments linked by living hinges;
deforming the body of the intervertebral implant about the living hinges from a first configuration whereby proximal and distal ends of the body are at a maximum separation along a lateral direction, to a second configuration whereby the proximal and distal ends are closer together along the lateral direction than in the first configuration; and
locking the body in the second configuration after the deforming step
wherein the body of the intervertebral implant is a circuitous body prior to the inserting step, the circuitous body having a lumen extending therethrough along a longitudinal direction that is perpendicular to the lateral direction.

15. The method of claim 14, further comprising the step of coupling an implantation tool to an aperture at the proximal end of the body.

16. The method of claim 15, wherein the coupling step comprises inserting prongs of the implantation tool into a pair of proximally extending slots at the proximal end.

17. The method of claim 14, further comprising the step of causing texture of at least one exterior surface of the body to enhance fixed contact with a respective at least one of the adjacent vertebrae.

18. The method of claim 14, wherein the deforming step causes a contact adhesive on one of the segments to attach the one of the segments to an adjacent one of the segments that combine to define one of the living hinges.

19. The method of claim 18, wherein the proximal and distal ends are opposite each other along a lateral direction perpendicular to the longitudinal direction.

* * * * *